US011045779B2

(12) United States Patent
Gozzini (10) Patent No.: US 11,045,779 B2
(45) Date of Patent: Jun. 29, 2021

(54) SHELL-AND-TUBE EQUIPMENT WITH DISTRIBUTION DEVICE (71) Applicant: ALFA LAVAL OLMI S.P.A., Suisio (IT)

(72) Inventor: Alberto Gozzini, Bergamo (IT)

(73) Assignee: ALFA LAVAL OLMI S.P.A, Suisio (IT)

( * ) Notice: Subject to any disclaimer, the term of this patent is extended or adjusted under 35 U.S.C. 154(b) by 0 days.

(21) Appl. No.: 16/759,219

(22) PCT Filed: Oct. 25, 2018

(86) PCT No.: PCT/EP2018/079356
§ 371 (c)(1),
(2) Date: Apr. 24, 2020

(87) PCT Pub. No.: WO2019/081686
PCT Pub. Date: May 2, 2019

(65) Prior Publication Data
US 2020/0306711 A1    Oct. 1, 2020

(30) Foreign Application Priority Data
Oct. 26, 2017 (EP) .................................... 17425106

(51) Int. Cl.
*B01J 4/00* (2006.01)
*B01J 19/24* (2006.01)
(Continued)

(52) U.S. Cl.
CPC .............. *B01J 4/005* (2013.01); *B01D 1/065* (2013.01); *B01D 3/008* (2013.01); *B01D 3/009* (2013.01);
(Continued)

(58) Field of Classification Search
CPC .. B01J 19/247; B01J 19/2425; B01J 19/0053; B01J 4/005; B01J 10/02; B01D 1/065;
(Continued)

(56) References Cited

U.S. PATENT DOCUMENTS 3,797,552 A    3/1974  Frank et al.
4,932,468 A *  6/1990  Ayub ........................ F28D 3/02
                                                    159/13.2
(Continued)

FOREIGN PATENT DOCUMENTS

CN    102805949 A    12/2012
EP      2246109 A1   11/2010
(Continued)

OTHER PUBLICATIONS

International Search Report (PCT/ISA/210) dated Nov. 29, 2018, by the European Patent Office as the International Searching Authority for International Application No. PCT/EP2018/079356.
(Continued)

*Primary Examiner* — Lessanework Seifu
(74) *Attorney, Agent, or Firm* — Buchanan Ingersoll & Rooney PC (57) ABSTRACT

A shell-and-tube equipment has a cylindrical geometry and is arranged along a vertical axis. The shell-and-tube equipment comprises an upper chamber and a lower chamber connected to a common tube bundle on opposite sides. The upper chamber is provided with at least an inlet nozzle for inletting a first fluid. The tube bundle is surrounded by a shell provided with nozzles for inletting and outletting a second fluid which exchanges heat with the first fluid through the tube bundle. The upper chamber encloses at least a distribution device configured for uniformly delivering the first fluid towards the tube bundle. The distribution device comprises an annular channel which is arranged (Continued)

around the vertical axis and is in fluid communication with the inlet nozzle. The distribution device comprises a plurality of channel modules of circular trapezoid shape, tightly joined together at their respective vertical edges for forming the annular channel.

15 Claims, 5 Drawing Sheets

(51) Int. Cl.
| | |
|---|---|
| *B01D 1/06* | (2006.01) |
| *B01D 3/00* | (2006.01) |
| *B01D 3/04* | (2006.01) |
| *B01J 10/02* | (2006.01) |
| *C07C 273/16* | (2006.01) |
| *F28D 7/12* | (2006.01) |
| *F28F 9/02* | (2006.01) |
| *F28D 21/00* | (2006.01) |

(52) U.S. Cl.
CPC ............... *B01D 3/04* (2013.01); *B01J 10/02* (2013.01); *B01J 19/247* (2013.01); *C07C 273/16* (2013.01); *F28D 7/12* (2013.01); *F28F 9/026* (2013.01); *B01J 2204/002* (2013.01); *B01J 2219/00081* (2013.01); *B01J 2219/185* (2013.01); *F28D 2021/0022* (2013.01)

(58) Field of Classification Search
CPC .......... B01D 3/008; B01D 3/009; B01D 3/04; C07C 273/16
See application file for complete search history.

(56) References Cited

U.S. PATENT DOCUMENTS

| | | |
|---|---|---|
| 6,089,312 A | 7/2000 | Biar et al. |
| 6,926,869 B2 | 8/2005 | Rizzi |
| 7,252,693 B2 | 8/2007 | Rostrup-nielsen et al. |
| 8,597,586 B2 | 12/2013 | Gerlinger et al. |
| 9,440,903 B2 | 9/2016 | DeCourcy et al. |
| 2012/0014847 A1 | 1/2012 | Killen et al. |
| 2012/0296120 A1 | 11/2012 | Scotto et al. |

FOREIGN PATENT DOCUMENTS

| | | |
|---|---|---|
| EP | 3037165 A1 | 6/2016 |
| JP | S613999 A | 1/1986 |
| JP | 2012-525244 A | 10/2012 |
| JP | 2013-538115 A | 10/2013 |
| TW | 201722550 A | 7/2017 |

OTHER PUBLICATIONS

Written Opinion (PCT/ISA/237) dated Nov. 29, 2018, by the European Patent Office as the International Searching Authority for International Application No. PCT/EP2018/079356.

Office Action (First Examination Report) dated Jan. 28, 2021, by the Intellectual Property India in corresponding India Patent Application No. 202017019140 with an English Translation of the Office Action. (6 pages).

Notice of Allowance (Decision to Grant a Patent) dated Apr. 19, 2021, by the Japanese Patent Office in corresponding Japanese Patent Application No. 2020-523360 and an English Translation of the Notice of Allowance. (5 pages).

* cited by examiner

SHELL-AND-TUBE EQUIPMENT WITH DISTRIBUTION DEVICE

BACKGROUND OF THE INVENTION

The present invention refers to a shell-and-tube equipment and, more specifically, to a urea stripper provided with an improved distribution device.

In a process for the production of urea, it is known to feed the urea solution coming from a urea reactor to a stripper, where the urea carbamate present in the solution is decomposed into ammonia and carbon dioxide with the help of heat and of a stripping agent.

A urea stripper is basically a vertical shell-and-tube heat exchanger, comprising an upper chamber and a lower chamber, in fluid communication by means of the tubes of a tube bundle. The upper chamber is fed with a first fluid, that is the urea reactor effluent consisting of a liquid solution containing urea and urea carbamate. The shell is fed with a second fluid, that is the hottest medium providing for the necessary heat. The lower chamber is fed by a third medium, that is a stripping gas which can be either carbon monoxide or ammonia. The lower chamber thus collects the concentrated urea solution from the tubes, that is a solution depleted from urea carbamate. As a result of the stripping, or decomposition of the urea carbamate, a gaseous phase comprising the stripping medium and the gases from carbamate decomposition is collected in the upper part of the upper chamber. In operation, the liquid urea solution forms a falling film on the inner surface of tubes, while the gaseous stripping medium flows in counter-current, i.e. from bottom to top, in the same tubes.

The performances of a urea stripper are very dependent from the regularity and uniformity of the falling film of the first fluid (urea and urea carbamate solution) in the tubes of the tube bundle. Therefore, the first fluid, once injected into the equipment through a respective nozzle located in the upper chamber, needs to be conveyed in a distribution device. The distribution device typically consists of a chamber with a circular crown shape. When the level of the fluid in the distributor device achieves the lowest border of the internal wall, it falls heavily on a distributor grid, so as to be uniformly directed to the tubes.

In the manufacturing phase of the shell-and-tube equipment, the distribution device usually needs to be inserted into the upper chamber through a manhole commonly provided at the top portion of said upper chamber. The manhole typically has an internal diameter of about 600 mm. Additionally, the distribution device needs to be inspected through the manhole for maintenance purposes, and sometimes the components of the distribution device should be disassembled for being extracted through said manhole.

A typical distribution device according to the prior art comprises a circular crown shaped base plate, a circular external wall with a predefined diameter and a circular internal wall, the diameter of which is smaller than the diameter of the circular external wall. Therefore, the circular external wall and the circular internal wall are concentrically arranged and define a crown shaped distribution chamber therebetween.

The base plate and each vertical wall are respectively made of a plurality of metal sheets that are joined together through a number of bolts. Additionally, each of these components, once manufactured, needs to be joined to the other components through further bolts. Teflon gaskets can be provided between the metal sheets, especially at the joining portion between the base plate and each vertical wall, to reduce possible, undesired slots and consequent leakages of the first fluid.

Accordingly, in such distribution device according to the prior art the base plate and each vertical wall are approached to one another and kept in place by the bolts. However, such an assembling cannot guarantee a perfect tightness. Therefore, due to mechanical tolerances and irregularities of the metal sheets and of the assembled distribution device, significant leakage of the first fluid, that is of urea and urea carbamate solution, actually occurs in said distribution device. In other words, with such a distribution device, an amount of the first fluid entering the equipment is correctly delivered to the distributor grid, whereas the remaining amount of this fluid wrongly flows through undesired slots or openings.

Document U.S. Pat. No. 7,252,693 describes a shell-and-tube reactor having a distribution chamber that encloses a distribution assembly. The distribution assembly is manufactured as a separate component with respect to the distribution chamber. The distribution assembly consists of a distribution sleeve provided with holes. The fluid is supplied as a falling film from the distribution chamber to the distribution sleeve through the holes.

Document U.S. Pat. No. 6,926,869 describes a urea stripper provided with a distribution box made of welded metal sheets. The task of such box is that of distributing the process ureic solution onto the underlying tube plate. However, such box is not provided with concentric circular vertical walls.

Document US 2012/296120 describes a urea stripper having a distribution device consisting of a perforated distribution tray and an intermediate grid. No concentric circular vertical walls are provided.

Document U.S. Pat. No. 8,597,586 describes a shell-and-tube reactor provided with a distributor plate having a polygonal cross section. No concentric vertical walls are provided for surrounding the distributor plate.

SUMMARY OF THE INVENTION

One object of the present invention is therefore to provide a shell-and-tube equipment with an improved distribution device which is capable of resolving the drawbacks of the prior art in a simple, inexpensive and particularly functional manner.

In detail, one object of the present invention is to provide a shell-and-tube equipment wherein the leakage in the respective distribution device is reduced as much as possible.

Another object of the present invention is to provide a shell-and-tube equipment wherein the fluid entering on the tube side is evenly distributed into the tubes of the tube bundle, so as to increase the performances of the equipment.

A further object of the present invention is to provide a shell-and-tube equipment where assembly is facilitated.

These objects are achieved according to the present invention by providing a shell-and-tube equipment with an improved distribution device as set forth in the attached claims.

Further characteristics of the invention are underlined by the dependent claims, which are an integral part of the present description.

BRIEF DESCRIPTION OF THE DRAWINGS

The characteristics and advantages of a shell-and-tube equipment with an improved distribution device according to the present invention will be clearer from the following exemplifying and non-limiting description, with reference to the enclosed schematic drawings, in which.

DETAILED DESCRIPTION OF THE PREFERRED EMBODIMENTS

Figure 1:
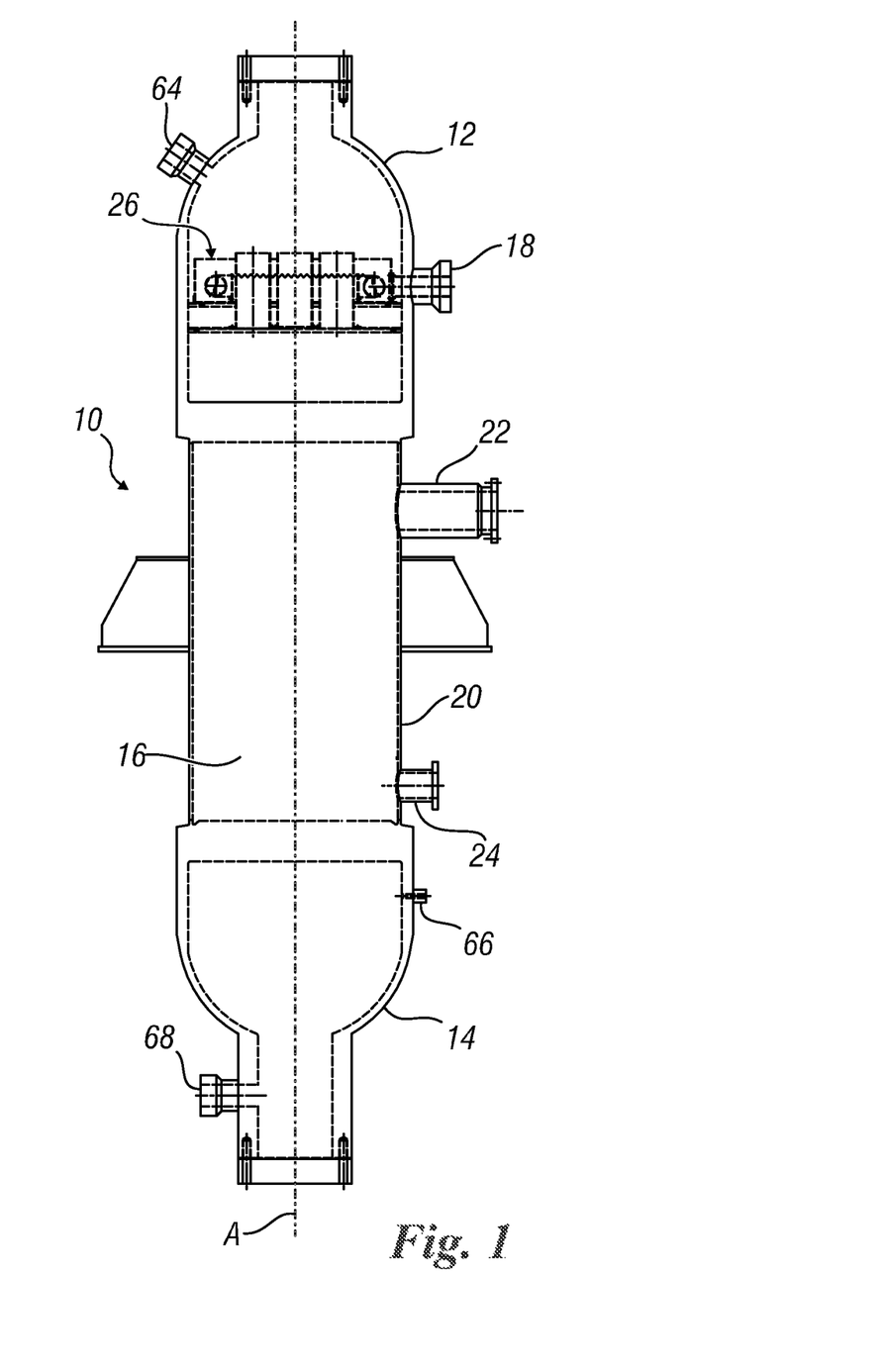
FIG. 1 schematically shows an embodiment of a shell-and-tube equipment with an improved distribution device according to the present invention.

With reference to FIG. 1, an embodiment of a shell-and-tube equipment 10 with an improved distribution device according to the present invention is shown. The equipment 10 has a cylindrical geometry and is arranged along a vertical axis A. The shell-and-tube equipment 10 comprises an upper chamber 12 and a lower chamber 14, connected on opposite sides by means of the tubes of a tube bundle 16. The upper chamber 12 and the lower chamber 14 are connected to the common tube bundle 16 on opposite sides. The upper chamber 12 and the lower chamber 14 are connected to the common tube bundle 16 on opposite sides of the tube bundle 16. The upper chamber 12 is connected to the tube bundle 16 at an upper end of the tube bundle 16 and the lower chamber 14 is connected to the tube bundle 16 at a lower end of the tube bundle 16. The upper end of the tube bundle 16 is connected to an upper tube sheet separating the upper chamber 12 from a space within the shell 20 surrounding the tube bundle 16. The upper end of the tube bundle 16 is typically welded to the upper tube sheet. The lower end of the tube bundle 16 is connected to a lower tube sheet separating the lower chamber 14 from the space within the shell 20 surrounding the tube bundle 16. The lower end of the tube bundle 16 is typically welded to the lower tube sheet.

The upper chamber 12 is provided with at least an inlet nozzle 18 for inletting a first fluid. The upper chamber 12 is also provided with at least an outlet nozzle 64, e.g. for outletting a third fluid, such as a stripping medium along with stripped species. The lower chamber 14 is provided with at least an inlet nozzle 66 for inletting the third fluid. The lower chamber 14 is also provided with at least an outlet nozzle 68, e.g. for outletting the first fluid, such as concentrated urea solution. The upper chamber 12 further encloses at least a distribution device 26 configured for uniformly delivering the first fluid towards the tubes of the tube bundle 16.

The tube bundle 16 is surrounded by a shell 20 provided with a primary nozzle 22 and a secondary nozzle 24 for inletting and outletting, respectively, a second fluid which exchanges heat with the first fluid through the walls of the tubes of the tube bundle 16. The second fluid, e.g. in the form of steam, is usually injected through the primary nozzle 22. The second fluid, e.g. in the form of water, is usually removed through the secondary nozzle 24. In a preferred embodiment of the shell-and-tube equipment 10, the first fluid is a urea and urea carbamate solution injected into the upper chamber 12, the second fluid is a heating medium flowing on the shell-side. The third fluid may be a stripping medium injected into the lower chamber 14. The shell-and-tube equipment 10 thus operates as a urea stripper for collecting, in the lower chamber 14, a concentrated urea solution from the tube bundle 16.

Figures 2, 2A:
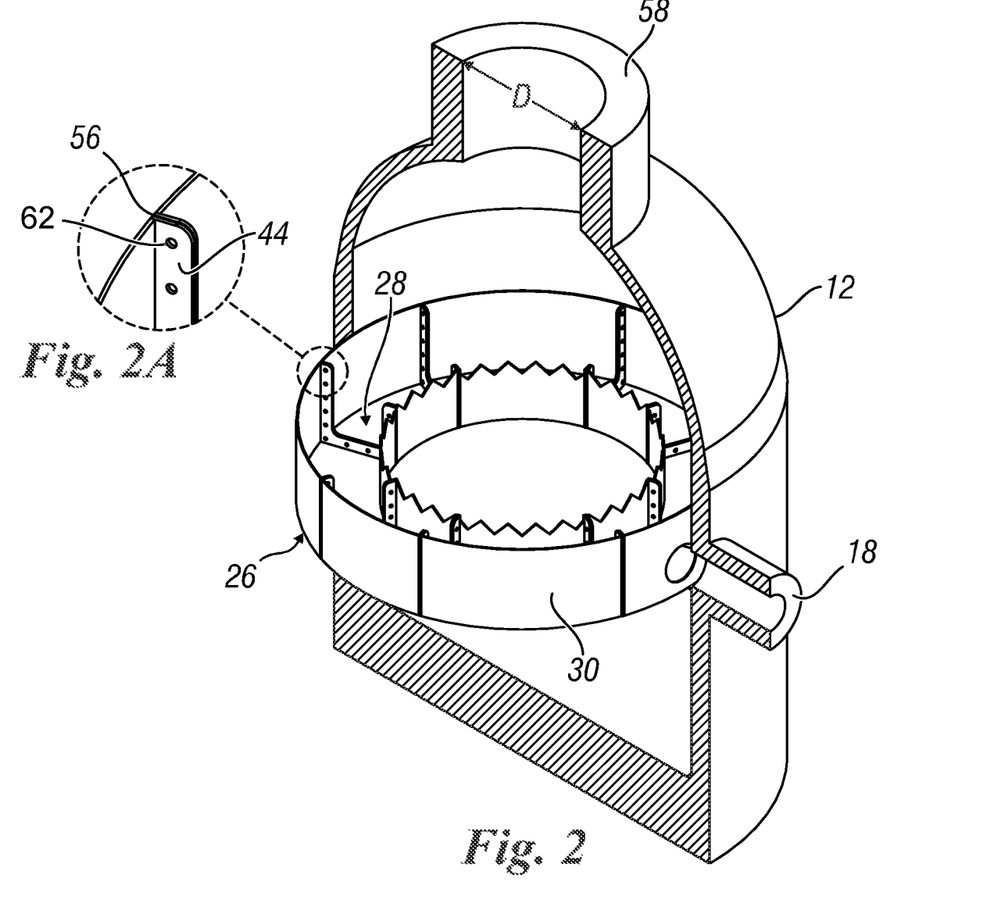
FIG. 2 is a sectional view of the upper chamber of the shell-and-tube equipment of FIG. 1, wherein a preferred embodiment of the distribution device according to the present invention is shown.
FIG. 2A is an enlarged view of a detail of the distribution device of FIG. 2.
Figure 3:
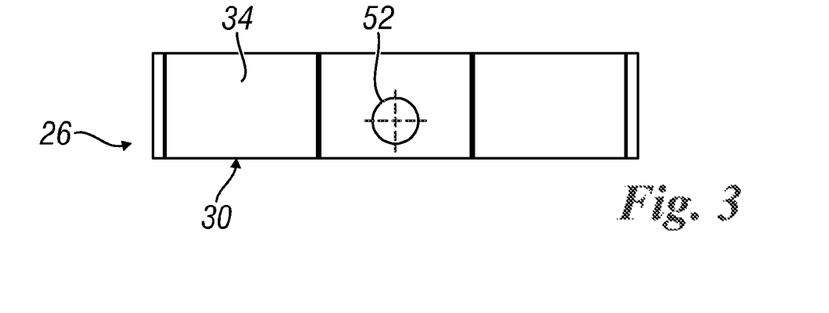
FIG. 3 is a plan view of the distribution device of FIG. 2.
Figure 4:
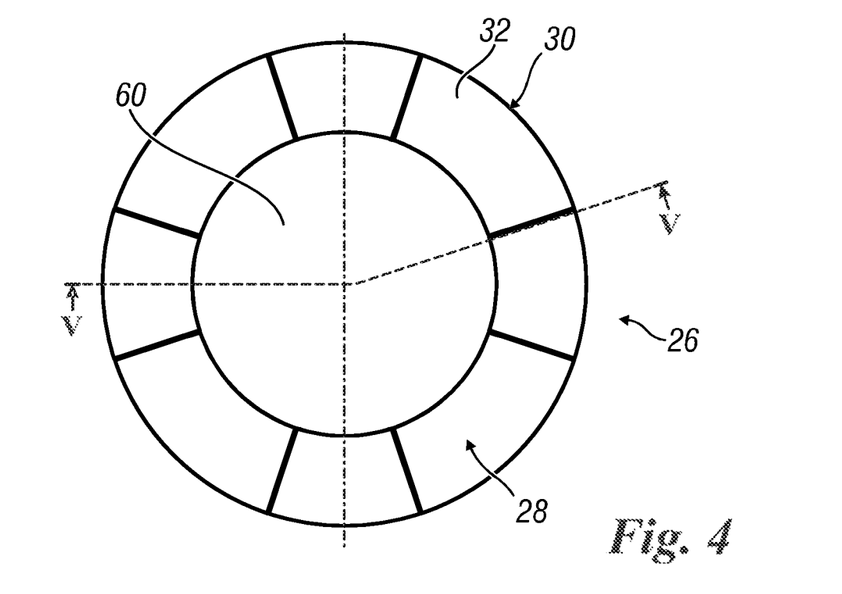
FIG. 4 is a top view of the distribution device of FIG. 2.
Figure 5:
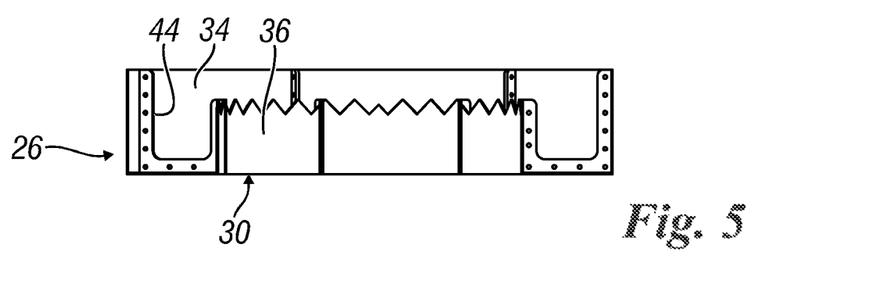
FIG. 5 is a sectional view, taken along the line V-V of FIG. 4, of the distribution device of FIG. 2.

The distribution device 26 comprises an annular channel 28 which is arranged around the vertical axis A and is in fluid communication with the inlet nozzle 18. According to the invention, the distribution device 26 comprises a plurality of channel boxes or modules 30 of circular trapezoid shape, tightly joined together at respective vertical edges 72, 74 of the channel modules 30 for forming the annular channel 28.

As shown in FIGS. 6-9, each channel module 30 comprises a horizontally arranged base plate 32, that is substantially perpendicular to the vertical axis A. Each base plate 32 is integral with an outer vertical wall 34, that forms the circumferential edge of the annular channel 28, and integral with an inner vertical wall 36, that is provided with an overflow edge 38 for the first fluid flowing towards the tubes of the tube bundle 16. An outer vertical edge 72 is arranged at each lateral end of the outer vertical wall 34. An inner vertical edge 74 is arranged at each lateral end of the inner wall 36.

According to a preferred embodiment of the invention, the base plate 32, the outer vertical wall 34 and the inner vertical wall 36 of each channel module 30 are joined together by welding at respective arc-shaped joining portions 40, 42. However, the base plate 32, the outer vertical wall 34 and the inner vertical wall 36 of each channel module 30 could also be made integral in another way, for example by metal casting in a proper mould.

Figure 8:
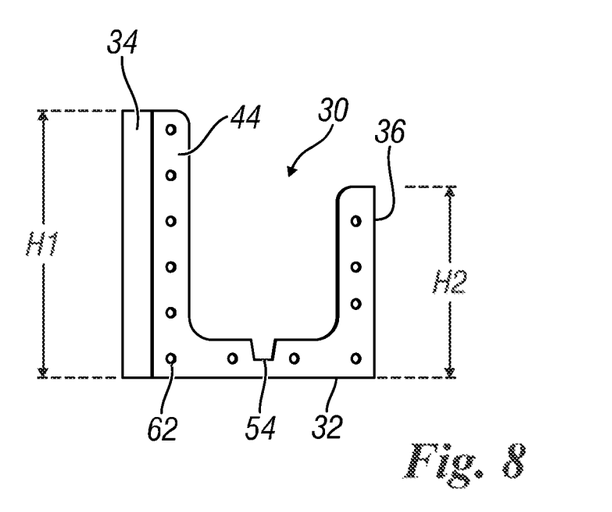
FIG. 8 is a side view of a single module of the distribution device of FIG. 2.
Figure 9:
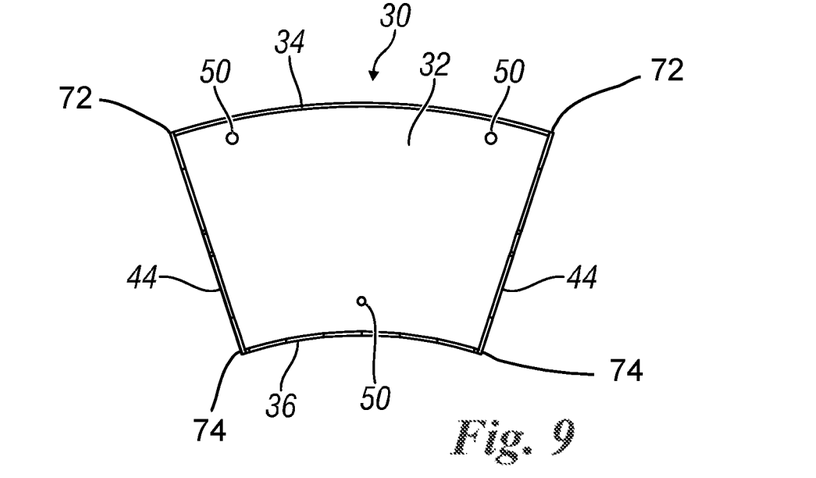
FIG. 9 is a top view of a single module of the distribution device of FIG. 2.

Preferably, as shown for example in FIG. 8, the outer vertical wall 34 of each channel module 30 has an overall height H1, measured along the vertical axis A, that is greater than the overall height H2 of the respective inner vertical wall 36. At least the smallest height, preferably the overall height, of the outer vertical wall 34 is larger than the smallest height of the inner vertical wall 36. The first fluid is thus capable of flowing towards the tubes of the tube bundle 16 through a central aperture 60 of the distribution device 26. The central aperture 60 is circular. The central aperture 60 can be provided with a perforated distributor plate (not shown) for evenly distributing the first fluid into the tubes of the tube bundle 16.

The overflow edge 38 of each vertical wall 36 can have a serrated or saw-shaped profile, that is, with alternated upwardly directed protrusions 46 and downwardly directed recesses 48. The protrusions 46 and the recesses 48 are preferably of triangular shape respectively. This specific design of the distribution device 26 improves the capabilities of the first fluid to be even distributed into the tubes of the tube bundle 16.

At least one of the channel modules 30 of the distribution device 26 can be provided, on the respective base plate 32, with at least a drainage through hole 50. Each drainage through hole 50 is closed with a respective cap (not shown) in the operational configuration of the shell-and-tube equipment 10. The purpose of the drainage through holes 50 is that of discharging the first fluid from the annular channel 28 of the distribution device 26 during the maintenance operations of the shell-and-tube equipment 10.

The fluid communication between the inlet nozzle 18 and the annular channel 28 of the distribution device 26 can be obtained with a through bore 52 obtained on the outer vertical wall 34 of one of the channel modules 30. The through bore 52 can be hydraulically connected with the inlet nozzle 18 by means of a tightly arranged connecting pipe.

Preferably, each channel module 30 of the distribution device 26 is provided with a flanged portion 44 on at least one of its respective vertical edges 72, 74. The flanged portions 44 of a single channel module 30 are configured for coupling with corresponding flanged portions 44 of adjacent channel modules 30. Each flanged portion 44 is preferably provided on the vertical edges 72, 74, i.e. on the vertical edges 72, 74 at one end of the channel module 30. Preferably, one flanged portion 44 is provided on the vertical edges 72, 74 of one lateral end of the channel module 30 and one flanged portion 44 is provided on the vertical edges 72, 74 of another lateral end of the channel module 30. The flanged portion 44 provided at one lateral end of the channel module 30 is configured for coupling with a flanged portion 44 provided at another lateral end of an adjacent channel module 30. The flanged portion 44 provided at another lateral end of the channel module 30 is configured for coupling with a flanged portion 44 provided at one lateral end of another adjacent module 30.

The flanged portion 44 comprises a flat surface facing a corresponding flat surface of an adjacent flanged portion 44. The flat surfaces of two adjacent channel modules 30 facing each other are parallel to each other. Preferably, the surface of the flanged portion 44 facing an adjacent channel module 30 is flat. More preferred, the flanged portion 44 is flat. The flanged portion 44 extends perpendicular to at least one of the base plate 32, the outer vertical wall 34 and the inner vertical wall 36. More precisely, the flanged portion 44 extends perpendicular to at least one of the base plate 32, a tangent of the outer vertical wall 34 at the joinder of the flanged portion 44 and the outer vertical wall 34 and a tangent of the inner vertical wall 36 at the joinder of the flanged portion 44 and the inner vertical wall 36. The flanged portion 44 is flat and extends in a plane parallel to the interface between two adjacent channel modules 30. The joinder of the flanged portion 44 and the outer vertical wall 34 is located at the outer vertical edge 72. The joinder of the flanged portion 44 and the inner vertical wall 36 is located at the inner vertical edge 74. The outer vertical edge 72 can also be seen as the joinder of the flanged portion 44 and the outer vertical wall 34. The inner vertical edge 74 can also be seen as the joinder of the flanged portion 44 and the inner vertical wall 36.

The flanged portion 44 is integral with at least one of the base plate 32, the outer vertical wall 34 and the inner vertical wall 36. The flanged portion 44 is welded to at least one of the base plate 32, the outer vertical wall 34 and the inner vertical wall 36. Alternatively, the flanged portion 44 is formed by bending the starting material of at least one of the base plate 32, the outer vertical wall 34 and the inner vertical wall 36. If the flanged portion 44 is formed by bending only one or two of the base plate 32, the outer vertical wall 34 and the inner vertical wall 36, the flanged portion 44 may be welded to the other of the base plate 32, the outer vertical wall 34 and the inner vertical wall 36. The flanged portion 44 is located inside the distribution device 26 delimited by the base plate 32, the outer vertical wall 34 and the inner vertical wall 36. In other words, the flanged portion 44 does not protrude outside the distribution device 26. The flanged portion comprises a first portion along the edge of the outer vertical wall 34 facing an adjacent channel module 30, a second portion along the edge of the inner vertical wall 36 facing an adjacent channel module 30 and a third portion along the edge of the base plate 32 facing an adjacent channel module 30. The first portion of the flanged portion 44 extends along the outer vertical edge 72. The second portion of the flanged portion 44 extends along the inner vertical edge 74. The first, second and third portions of the flanged portion 44 extend along the full length of their respective edges.

Each flanged portion 44 is provided with at least a through hole 62 for the insertion of a respective coupling bolt provided with a nut. Preferably, a plurality of through holes 62 is provided on each flanged portion 44, whereas the number of bolt/nuts could be adjusted to find the best span between adjacent channel modules 30.

At least a sealing element 56 is provided between the respective flanged portions 44 of two adjacent channel modules 30. Preferably, each sealing element 56 comprises a vertically arranged gasket, which may be made of Teflon. With this specific design of the distribution device 26 all the discontinuities between adjacent channel modules 30 lay on a single plane, i.e. a vertical plane, and not on perpendicular plans.

Each Teflon gasket 56, being completely inserted into the internal side of the distribution device 26, can seal adequately. In other words, any leakage of the first fluid that can occur through each bolt and nut remains inside the distribution device 26. On the contrary, in the current traditional design of the distribution devices the discontinuities are due to the joint of perpendicular plates, that cannot be sealed properly with gaskets.

Figure 6:
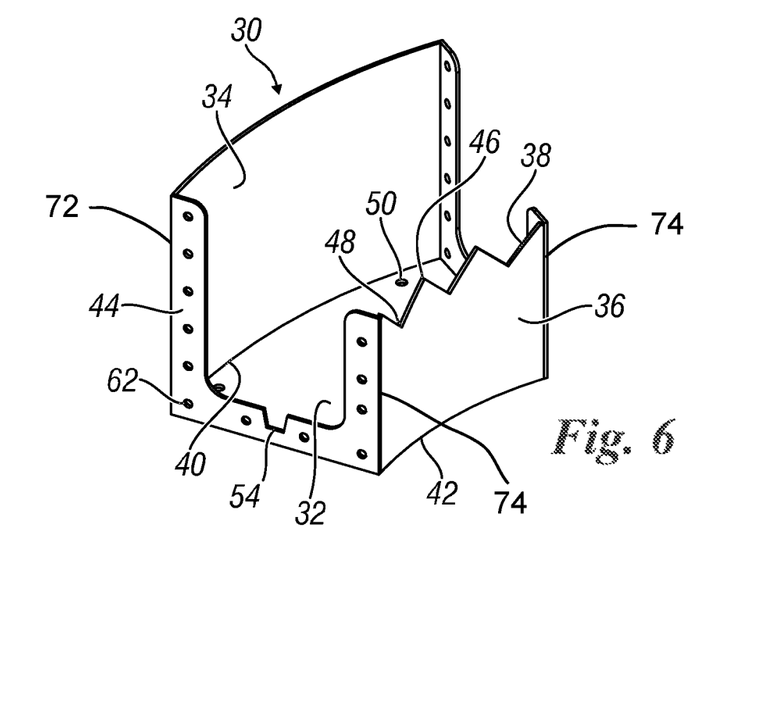
FIG. 6 is a perspective view of a single module of the distribution device of FIG. 2.
Figure 7:
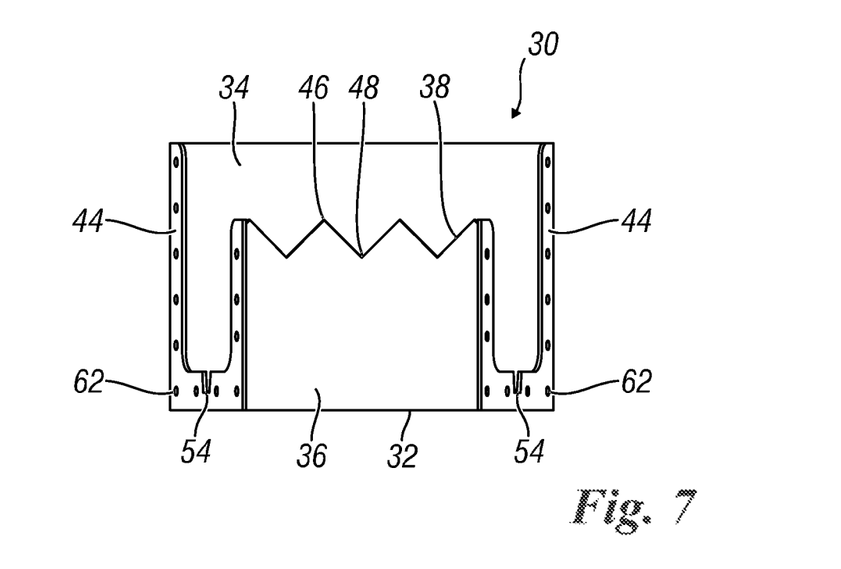
FIG. 7 is a front view of a single module of the distribution device of FIG. 2.

The flanged portions 44 can be provided with at least a notch 54 arranged at the bottom of the annular channel 28, as shown for example in FIGS. 6 and 8. Alternatively, the flanged portions 44 can be provided with a through hole arranged at the bottom of the annular channel 28. The notches 54 or through holes facilitate the flow of the first fluid through adjacent flanged portions 44 when the fluid level in the annular channel 28 is particularly low. In other words, the notches 54 or through holes are capable of reducing the residual fluid level in the annular channel 28 without affecting the tightness of the various channel modules 30.

As shown in FIG. 2, the upper chamber 12 of the shell-and-tube equipment 10 is typically provided on top with a circular opening or manhole 58 of predefined diameter D. The circular opening 58 is normally closed in the operational configuration of the shell-and-tube equipment 10, but it can be opened for maintenance purposes.

Preferably, each channel module 30 has a respective overall width that is smaller than the predefined diameter D of the circular opening 58. In this way, during the assembly phase of the shell-and-tube equipment 10, each channel module 30 can be inserted into the upper chamber 12 through the circular opening 58. Additionally, for maintenance purposes, each channel module 30 can be extracted from the upper chamber 12 through the circular opening 58 without disassembling the shell-and-tube equipment 10. The overall width of a channel module 30 is considered as the largest dimension of the channel module 30 as seen basically perpendicular to the longitudinal direction of the channel module 30.

Independently from the respective overall width, the number of channel modules 30 could be adjusted case by case considering the equipment 10 dimension and the weight of each single channel module 30. In addition, the distribution device 26 according to the present invention is self-supporting, then the assembly operation and the respective supporting structure (not shown in the drawings) could be simplified and made safer.

It is thus seen that the shell-and-tube equipment with an improved distribution device according to the present invention achieves the previously outlined objects.

The shell-and-tube equipment with an improved distribution device of the present invention thus conceived is susceptible in any case of numerous modifications and variants, all falling within the same inventive concept; in addition, all the details can be substituted by technically equivalent elements. In practice, the materials used, as well as the shapes and size, can be of any type according to the technical requirements.

The scope of protection of the invention is therefore defined by the enclosed claims.

The invention claimed is:

1. Shell-and-tube equipment having a cylindrical geometry and arranged along a vertical axis, the shell-and-tube equipment comprising an upper chamber and a lower chamber connected to a common tube bundle on opposite sides, wherein the upper chamber is provided with at least an inlet nozzle for inletting a first fluid, wherein the tube bundle is surrounded by a shell provided with nozzles for inletting and outletting a second fluid which exchanges heat with said first fluid through said tube bundle, and wherein the upper chamber encloses at least a distribution device configured for uniformly delivering said first fluid towards said tube bundle, said at least a distribution device comprising an annular channel which is arranged around said vertical axis and is in fluid communication with said at least an inlet nozzle, said at least a distribution device comprising a plurality of channel modules each possessing a circular trapezoidal shape and each including spaced apart vertical edges at opposite ends of the channel module, adjacent ones of the plurality of channel modules being joined together at the vertical edges of the adjacent channel modules so that the plurality of channel modules together form said annular channel.

2. Shell-and-tube equipment according to claim 1, wherein each channel module comprises a horizontally arranged base plate, integral with an outer vertical wall, forming the circumferential edge of said annular channel, and with an inner vertical wall, provided with an overflow edge for said first fluid flowing towards said tube bundle.

3. Shell-and-tube equipment according to claim 2, wherein said base plate, said outer vertical wall and said inner vertical wall are joined together by welding at respective arc-shaped joining portions.

4. Shell-and-tube equipment according to claim 2, wherein said outer vertical wall has an overall height, measured along said vertical axis, that is greater than the overall height of said inner vertical wall.

5. Shell-and-tube equipment according to claim 2, wherein said overflow edge has a serrated profile, with alternated upwardly directed protrusions and downwardly directed recesses.

6. Shell-and-tube equipment according to claim 2, wherein said base plate is provided with at least a drainage through hole which is closed with a respective cap in the operational configuration of the shell-and-tube equipment.

7. Shell-and-tube equipment according to claim 2, wherein at least one channel module is provided with a through bore on its respective outer vertical wall, said through bore being in fluid communication with said at least an inlet nozzle.

8. Shell-and-tube equipment according to claim 1, wherein each channel module is provided with a flanged portion on at least one of its respective vertical edges, said flanged portion being configured for coupling with a corresponding flanged portion of an adjacent channel module.

9. Shell-and-tube equipment according to claim 8, wherein the flanged portion comprises a flat surface facing a corresponding flat surface of an adjacent flanged portion.

10. Shell-and-tube equipment according to claim 8, wherein said flanged portion is provided with at least a through hole for the insertion of a respective coupling bolt.

11. Shell-and-tube equipment according to claim 8, wherein said flanged portion is provided with at least a notch arranged at the bottom of said annular channel, said notch facilitating the flow of said first fluid through adjacent flanged portions.

12. Shell-and-tube equipment according to claim 8, wherein said distribution device is provided with at least a sealing element between the respective flanged portions of two adjacent channel modules.

13. Shell-and-tube equipment according to claim 12, wherein said sealing element is a vertically arranged gasket.

14. Shell-and-tube equipment according to claim 1, wherein said upper chamber is provided on top with a circular opening of predefined diameter, each of said channel modules having a respective overall size that is smaller than said predefined diameter, so as to perform the insertion of each channel module into said upper chamber and/or the extraction of each channel module from said upper chamber through said circular opening.

15. Shell-and-tube equipment according to claim 1, wherein said first fluid is a urea and urea carbamate solution and said second fluid is a heating medium, wherein the lower chamber is provided with at least an inlet nozzle for inletting a third fluid consisting of a stripping medium, said shell-and-tube equipment thus operating as a urea stripper for collecting, in said lower chamber, a concentrated urea solution from said tube bundle.

* * * * *